United States Patent [19]

Liu

[11] Patent Number: 4,686,860

[45] Date of Patent: Aug. 18, 1987

[54] SELF-ALIGNING HYDRAULIC PISTON ASSEMBLY FOR TENSILE TESTING OF CERAMIC

[75] Inventor: Kenneth C. Liu, Oak Ridge, Tenn.

[73] Assignee: The United States of America as represented by the United States Department of Energy, Washington, D.C.

[21] Appl. No.: 853,106

[22] Filed: Apr. 17, 1986

[51] Int. Cl.[4] .............................................. G01N 3/02
[52] U.S. Cl. ........................................ 73/856; 73/837
[58] Field of Search ................. 73/808, 826, 831, 856, 73/813, 834, 837; 403/57, 58

[56] References Cited

U.S. PATENT DOCUMENTS 4,081,992  4/1978  Aurora et al. .......................... 73/84

FOREIGN PATENT DOCUMENTS 951104  8/1982  U.S.S.R. ................................ 73/826

OTHER PUBLICATIONS

Lange, F. F. et al., Powder-Cushion Gripping... Testing, Journal of Testing and Evaluation, vol. 6, No. 5, Sep. '78, pp. 320-323.
Pears, C. D., Structural Ceramics and Testing of Brittle Materials, Proceedings of Illinois Institute of Tech. Research Inst., Mar. '67, pp. 139-189.

Primary Examiner—Jerry W. Myracle
Attorney, Agent, or Firm—Stephen D. Hamel; Judson R. Hightower

[57] ABSTRACT

The present invention is directed to a self-aligning grip housing assembly that can transmit an uniaxial load to a tensil specimen without introducing bending stresses into the specimen. Disposed inside said grip housing assembly are a multiplicity of supporting pistons connected to a common source of pressurized oil that carry equal shares of the load applied to the specimen irregardless whether there is initial misalignment between the specimen load column assembly and housing axis.

3 Claims, 4 Drawing Figures the housing assembly for gripping the end of the ceramic specimen.

The fluid pressure will vary proportionally when the load is applied through the pull rod. Little or no displacement of the pistons or pull rod assembly will occur because the hydraulic fluid is virtually incompressible. Therefore, friction within the grip system is negligible.

Use of hydraulic fluid as a distribution medium to divide the applied load into a multiplicity of equal parts counteracted by the circular array of miniature pistons is a key feature of the invention. Since the pistons are equally spaced on the circle, and piston forces are equal because they are connected to a common oil distribution manifold, the net sum of the first moments resulting from the piston forces with respect to any arbitrary diameter passing through the center of the piston circle must be equal to zero. This zero first moment implies that the applied force is in perfect alignment with the center of the piston circle.

Other and further objects of the invention will be obvious upon an examination of the illustrative embodiment (or method) about to be described or will be indicated in the appended claims, and various advantages not referred to herein will occur to our skilled in the art upon employment of the invention in practice.

DETAILED DESCRIPTION OF THE INVENTION

As briefly mentioned above, the present invention is directed to providing a self-aligning grip for transmitting an uniaxial load to a tensile specimen. The grip system consists of eight individual supporting pistons that carry equal shares of the load being applied to the pull rod, thus allowing the reactive loads to be measured directly with load transducers.

Figure 1:
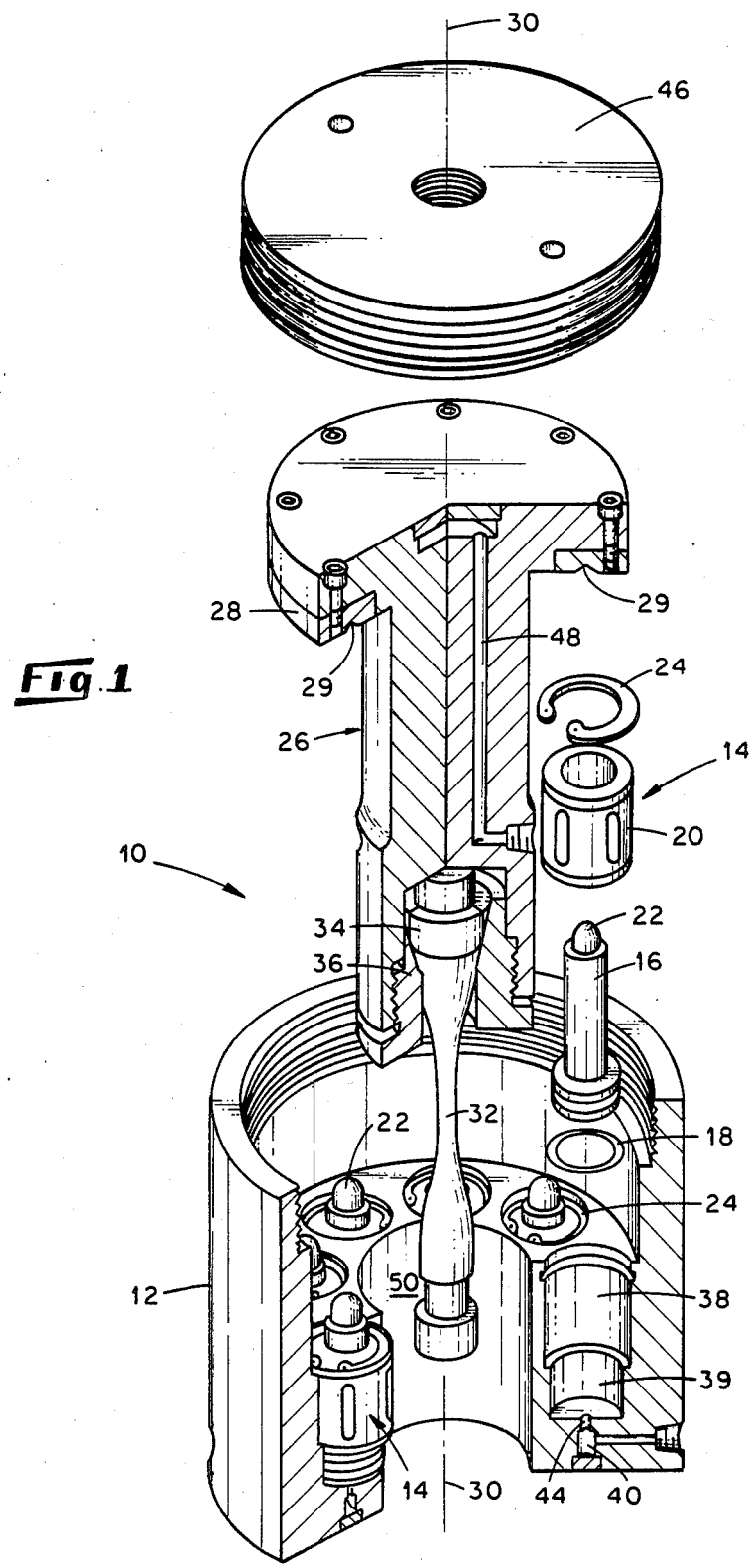
FIG. 1 is an exploded isometric view, partially cross sectioned of the self aligning grip in accordance with the present invention.

Described in general detail and with reference to the accompanying drawings, the self-aligning grip assembly is shown at 10 in FIG. 1. Self-aligning grip assembly 10 includes support housing 12 which accommodates a circular array of miniature hydraulic cylinder-piston assemblies 14. Hydraulic cylinder-piston assemblies 14 each consist of a piston 16, "0" ring seal 18, ball bearing bushing 20, and hemispherical cap 22. Each cylinder-piston assembly 14 is locked into cavities 38 in support housing 12 by means of a locking ring 24.

Pull rod assembly 26 and integral bearing cap 28 are supported on hemispherical caps 22 of the array of cylinder-piston assemblies in such a manner that the resultant force is always centered around centerline 30. The button head ceramic specimen 32 is attached to pull rod assembly 26 by means of a tapered split collar 34 and compression nut 36 being threaded into the lower end of pull rod assembly 26.

Figure 2:
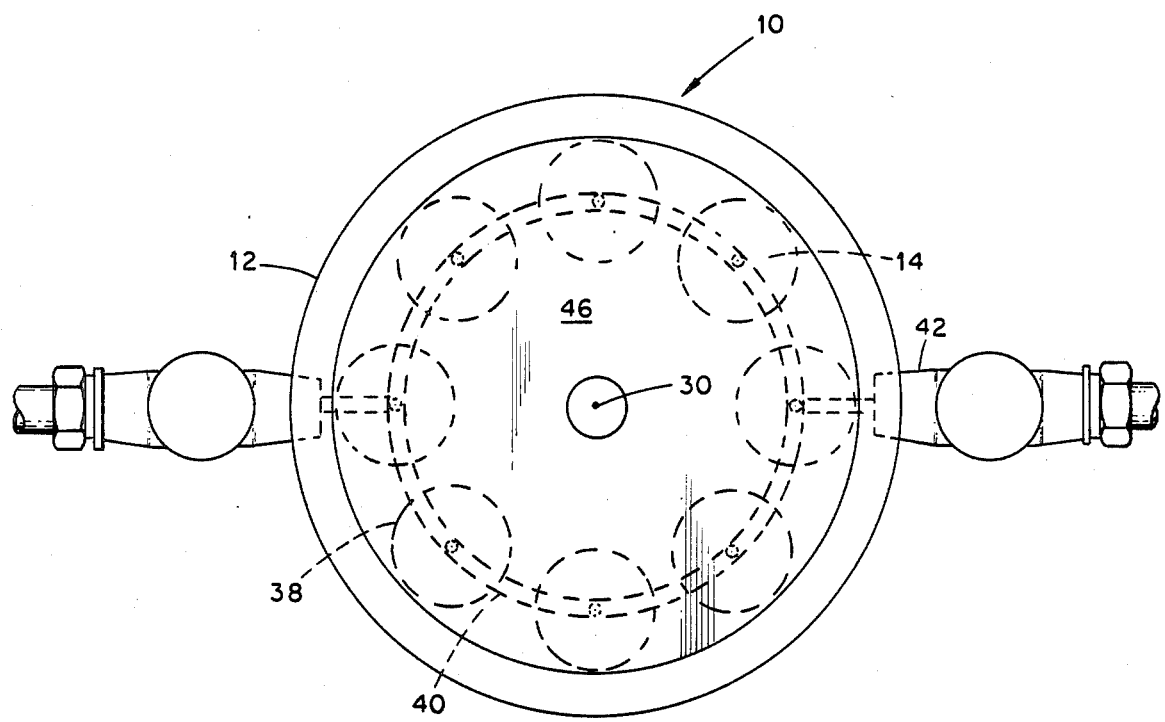
FIG. 2 is a plan view of the self aligning grip and support housing.

Referring now to FIG. 2, eight identical cylinder assemblies 14, fixedly mounted into cavities 38 are equally spaced in housing 12 in a circular array around centerline 30. The oil chambers 39 at the bottom of

SELF-ALIGNING HYDRAULIC PISTON ASSEMBLY FOR TENSILE TESTING OF CERAMIC

The invention was made as a result of work done under Contract DE-AC05-840R21400 with Martin Marietta Energy Systems, Inc., and the U.S. Department of Energy.

BACKGROUND OF THE INVENTION

The present invention relates generally to a self-aligning grip housing and load train column assembly by which a uniaxial load can be transmitted through the centerline of a ceramic tensile specimen without introducing bending stresses.

Recent developments in ceramic materials have substantially advanced the state of the art and have resulted in the development of interest in such materials for use in heat engines and high-temperature conversion systems such as gas turbines.

Because the fractural strength of structural ceramics is vitally important to their use as engineering structural materials, means for accurately testing the tensile strength of ceramic specimens are needed to evaluate and characterize newly developed ceramic materials. Tensile testing of ceramics is inherently difficult due to the concentric load transfer (the avoidance of bending stresses in the specimen) being very critical to the accuracy of the test results.

Limited success in concentric load transfer to ceramic specimens during tensil testing has been achieved through the use of universal joints or equivalent mechanisms to avoid the occurrence of specimen bending from the loading mechanism. A set of lubricated hemispherical bearings has been used in the load train for ceramic tensile measurements in an attempt to eliminate all bending moments in the test specimen. The use of flexible cable to transmit loads has also provided a degree of success. There remains however a need for a simple economical procedure for measuring tensile cyclic fatigue properties of ceramics with little or no bending stresses being transmitted to the ceramic specimen during testing.

It is accordingly a general object of this invention to provide means for accurately testing the tensil strength of ceramic specimens. Another, more particular object of the invention is to provide a means for loading a ceramic specimen during a tensile test with little or no bending stresses being transmitted to the specimen.

SUMMARY OF THE INVENTION

In accordance with the invention a self-aligning grip system is provided for use in tension-tension dynamic fatigue testing of a uniaxially loaded ceramic specimen. The grip system consists of two major components: a hydraulic housing assembly and a pull rod assembly. A multiplicity of hydraulic piston assemblies are equally spaced in the hydraulic housing assembly on a circle about the centerline of the tensile specimen. The hydraulic piston assemblies are interconnected by oil channels that are part of an oil distribution manifold. With the piston oil chambers interconnected, the fluid pressure thus becomes uniform in the system. The pull rod assembly is provided with a circular flange which rests on the top of the piston assemblies and a pull rod which extends downwardly through the center hole of cavities 38 are interconnected by circular oil channel 40 which is part of manifold system 42. As shown in FIG. 1, the hydraulic fluid flows freely into oil chambers 39 through vertical needle holes in ports 44 in communication with channel 40. The assembled self-aligning grip system 10 has cover plate 46 screwably fixed into support housing 12.

In operation for room-temperature testing, the button-head fatigue specimen 32 is directly connected to metal pull rod assembly 26 by means of tapered split collar 34 and compression nut 36. This is a highly reliable gripping technique previously used in the art. For high temperature testing the pull rod may be cooled by water flowing through cooling channel 48 built into the rod stem.

The self-aligning grip is assembled by slipping pull rod assembly 26 with button-head specimen 32 attached downwardly into the center hole 50 of housing 12. Thus bearing head 28 with an annular v-shaped groove 29 rests on hydraulic piston heads 22 with groove 29 being positioned to be in radial alignment with respective hemispherical caps 22. Groove 29 provides a self-centering feature which positions pull rod assembly 26 centerally within housing 12 said cover plate 46 thusly completes the assembly.

Figure 4:
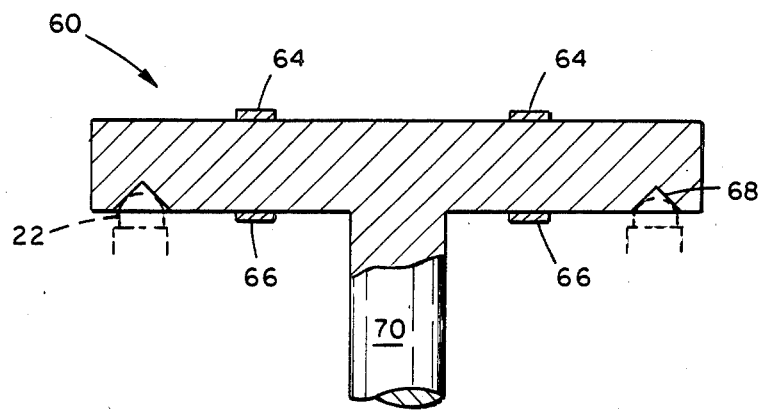
FIG. 4 is an elevational view of the calibrating pull rod.
Figure 3:
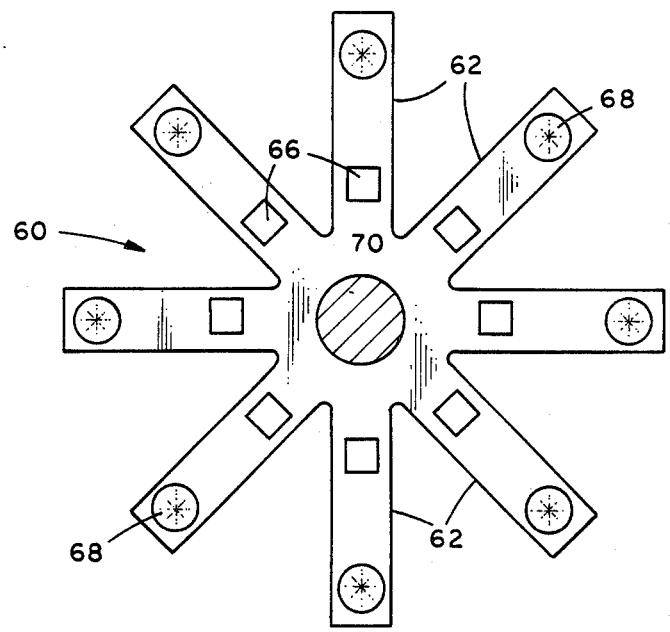
FIG. 3 is a plan view of the special pull rod transducer used for calibrating and evaluating the system.

Now turning to FIGS. 3 and 4, a special pull-rod assembly 60 was devised for the sole purpose of calibrating the system and demonstrating the uniformity of the reactive loads. The pull rod assembly 60 was provided with eight (one for each cylinder-piston assembly) cantilevered arms 62 which where instrumented with a pair of precision, precalibrated strain gages 64–66. Each cantilevered arm has a conical shaped precision machined recess 68 corresponding to groove 29 in the bearing head 28 illustrated in FIG. 1. Centrally located between said arms 62 is pull rod 70.

In a calibration operation, pull rod assembly 60 is placed within bore 50 with recesses 68 resting on corresponding hemispherical caps 22. When a load "P" is applied to pull rod 70, each hydraulic piston assembly 14 thus bears one-eighth of the total load "P". The total load "P" is measured by a load cell and the strain gages 66 measure the bending moment resulting from the reactive forces applied to the end of the cantilevered beam 62. The the signal outputs of the load cell and strain gage bridge circuits are monitored continuously by a data acquisition system. Results showed that the maximum deviation from the average values of the reactive loads being measured was less 0.5% at a full scale load of 5,000 lbs. On the basis of this data, the eccentricity of the resultant load thus is calculated to be less than 0.001 inch. These results confirm that a practical uniform-stress loading in tension is possible using this self-aligning hydraulic grip system to perform testing of ceramic materials.

The above description of a preferred embodiment of the invention should not be interpeted in a limiting sense. For example, the number of cylinder - piston assemblies could be varied from the eight illustrated. Also the exact specimen gripping technique illustrated is not critical and could be replaced with other equivalent, techniques without departing from the scope of the invention. It is intended rather that the invention be limited only by the claims appended hereto.

I claim:

1. A grip for tensile testing of ceramic specimens comprising:
    (a) an annular support housing defining a central cavity;
    (b) a multiplicity of hydraulic cylinder-piston assemblies equally spaced in a concentric circular array within said support housing about said central cavity;
    (c) a means for supplying pressurized oil to each of said hydraulic cylinder-pistons at the same oil pressure; and
    (d) a pull rod having a flanged end resting on said cylinder-piston assemblies and a gripper end for gripping said ceramic tensile specimen; said pull rod extending through said central cavity in said support housing.

2. The grip for claim 1 wherein said cylinder-piston assemblies are each provided with a hemispherical load cap and said flanged end of said pull rod is provided with a v-shaped groove in axial alignment with said load caps; said groove interacting with said load caps to center said pull rod in said support housing.

3. The grips of claim 1 wherein said housing defines an annular channel and a multiplicity of ports extending between said channel and said respective cylinder-piston assemblies to provide a common source of pressurized oil to said cylinder-piston assemblies.

* * * * *